United States Patent [19]

Furlong et al.

[11] Patent Number: 4,823,593
[45] Date of Patent: Apr. 25, 1989

[54] FLUERIC PARTIAL PRESSURE SENSORS

[75] Inventors: Owen D. Furlong, East Coker, Nr. Yeovil; Searle, Robin H. J., Hardington Mandeville, both of England

[73] Assignee: Normalair-Garrett (Holdings) Limited, Somerset, England

[21] Appl. No.: 127,419

[22] Filed: Dec. 2, 1987

[30] Foreign Application Priority Data

Dec. 8, 1986 [GB] United Kingdom ............ 8629264
Dec. 8, 1986 [GB] United Kingdom ............ 8629265
Dec. 8, 1986 [GB] United Kingdom ............ 8629266
Jun. 1, 1987 [GB] United Kingdom ............ 8712797

[51] Int. Cl.$^4$ ............................................. G01N 7/00
[52] U.S. Cl. ................................... 73/23; 128/204.24; 137/804
[58] Field of Search .......... 73/23; 128/204.24, 204.29, 128/205.11; 137/828, 804, 835, 81.1, 840; 236/101 R, 102

[56] References Cited

U.S. PATENT DOCUMENTS

| | | | |
|---|---|---|---|
| 2,439,336 | 4/1948 | Dillman | 236/101 R |
| 2,570,432 | 10/1951 | Dillon | 236/101 R |
| 3,121,331 | 2/1964 | Von Platen | 236/101 R |
| 3,540,463 | 11/1970 | Meyer | 137/804 |
| 3,980,103 | 9/1976 | Drzewiecki | 137/828 |
| 4,246,935 | 1/1981 | Mon | 137/840 |
| 4,407,153 | 10/1983 | Furlong et al. | 73/23 |
| 4,451,002 | 5/1984 | Klee et al. | 236/101 R |
| 4,596,360 | 6/1986 | Cohen | 236/102 |
| 4,606,497 | 8/1986 | Heimovics, Jr. | 236/101 R |

*Primary Examiner*—Stewart J. Levy
*Assistant Examiner*—Laurence G. Fess
*Attorney, Agent, or Firm*—Larson and Taylor

[57] ABSTRACT

The temperature range for stable operation of a flueric partial pressure sensor (300) is improved by temperature-responsive means (80, 60) which vary with temperature change the suction applied by a flueric aspirator (27) in drawing gas through sensor bridge legs (12, 13) and a power line (37) of a flueric amplifier (11). The temperature-responsive means may comprise temperature-sensitive adjustment means (107, FIG. 2) embodied in a pressure reducing valve (80) to vary the pressure of working gas supplied by way of delivery line (28) for driving the flueric aspirator. Alternatively or additionally the temperature-responsive means may comprise a temperature-sensitive bleed valve (60) incorporated in a common outlet (14) from the bridge legs and the flueric amplifier power line. Further improvement at the low temperature end of the working range may be obtained by incorporating pressure reducing means such as a linear flow resistor 120) in the supply line (30) to the main power jets (31, 32) of the flueric amplifier.

12 Claims, 5 Drawing Sheets

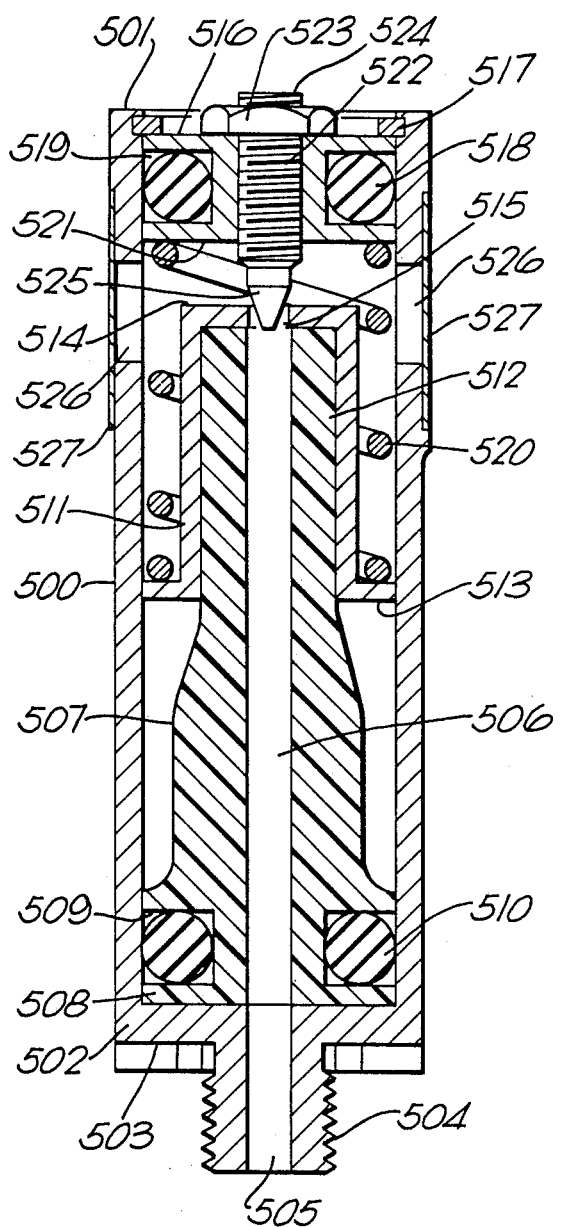

FLUERIC PARTIAL PRESSURE SENSORS

BACKGROUND OF THE INVENTION

1. Field of the Invention

This invention relates to flueric partial pressure sensors and is more particularly, but not exclusively, concerned with a flueric partial pressure sensor for sensing the partial pressure of oxygen in oxygen enriched air in varying or variable ambient pressure conditions.

2. Description of the Prior Art

It is necessary for a certain minimum oxygen pressure to exist in the lungs for the oxygen to be able to diffuse through the lung tissue and pass to the haemoglobin or red corpuscles in the blood. However, the partial pressure of oxygen in the atmosphere falls off with altitude in direct proportion to the absolute pressure value. This problem must be overcome in aircraft breathing systems so as to provide aircrew with breathing air having a substantially constant partial pressure of oxygen value. In order to maintain a sea level oxygen partial pressure value of 160 mm Hg the level of oxygen concentration in the breathing air must increase from 21% by volume in air at sea level to about 65% by volume in air at 9000 meters (30000 feet).

EP-A-No. 0,036,285 and corresponding U.S. Pat. No. 4,407,153 (Normalair-Garrett) disclose a flueric partial pressure sensor including a flueric bridge having two bridge legs adapted for sensing a reference gas and a sample-gas mixture. A linear resistor and an orifice resistor are incorporated in each of the bridge legs which are conjoined to discharge from a single outlet. Reference gas and sample-gas mixture are drawn through the respective legs of the bridge by connecting the conjoined outlet to a small flueric aspirator or ejector arranged for operation in the manner of a jet pump by a clean dry gas which may conveniently be the reference gas supplied by way of a pressure reducing valve. Reference gas and sample-gas mixture are supplied to the bridge legs by way of shrouded filters which are open to the same ambient pressure so that pressure difference across each of the bridge legs is the same under all conditions of use. The resistors are arranged to provide an asymmetric balance of the flow rates through the bridge legs, the asymmetric balance being selected so that in operation the bridge output signal, in terms of differential pressure, is constant for a chosen partial pressure of a constituent gas such as oxygen in a sample-gas mixture, for example oxygen-enriched air, in varying absolute pressure conditions such as changes in altitude. Respective pressure signal outlets are connected one with each bridge leg at a position between the linear resistor and the orifice resistor. The bridge output signal is amplified by a flueric laminar flow proportional amplifier which is driven by being connected to the flueric aspirator at the conjoined outlet of the bridge legs. This amplified signal may be used for a number of purposes including control of a switching device or in providing a visual and/or audible warning signal.

An example of use of this flueric partial pressure sensor is the control of a molecular sieve type gas separation system (MSOGS) embodied in an aircraft on-board oxygen generating system (OBOGS) delivering oxygen-enriched air for breathing by aircrew such as is disclosed in EP-A-No. 0,129,304 and corresponding U.S. patent application Ser. No. 595,303 (Normalair-Garrett). The system comprises three molecular sieve beds which in operation are cyclically subjected to a charge/adsorption on-stream phase followed by a purge/desorption regeneration phase. A fixed logic sequencer provides two different overall cycle times and fixes the relative durations of each phase within the overall cycle times. The flueric partial pressure sensor is connected into the system and arranged to receive as its sample-gas mixture a bleed of oxygen-enriched air delivered by the MSOGS. The flueric partial pressure sensor senses the oxygen concentration in the oxygen-enriched air and switches the fixed logic sequencer between the two cycle times so as to obtain an oxygen concentration necessary to maintain the partial pressure of oxygen in the oxygen-enriched air delivered by the MSOGS at a predetermined set point value for the flueric bridge of the sensor irrespective of changes in cabin altitude between sea level and 7600 meters (25000 feet).

The flueric partial pressure sensor has proven completely satisfactory in maintaining oxygen concentration within required minimum and maximum bands through an operational range of aircraft cabin altitude ranging from sea level to 7600 meters (25000 feet) and cabin temperatures ranging from +5° C. to +35° C. However, there is now a requirement to expand the operational temperature range at both the upper and lower ends.

Temperature tests carried out in an altitude chamber have shown the flueric partial pressure sensor to become unstable in operation at temperatures below about −5° C. particularly when operating at altitudes below 2000 meters (7000 feet). These tests have also shown that operation of the amplifier is affected with increasing temperature so that the amplifier gain is progressively reduced particularly under high altitude conditions.

Intensive study, including considerable mathematical analysis, has led towards the conclusion that the problem at the low temperature end results from the flow in the internal flow passages of the amplifier becoming turbulent due to the value of the Reynolds number for the main power jets increasing beyond a critical value of just over 1000 as temperature falls. On the other hand, with increasing temperature and altitude the Reynolds number decreases and tests have shown that the working Reynolds number for the main power jets of the amplifier falls to a value at which the amplifier signal gain is reduced so as to cause malfunctioning of a MSOGS or warning system controlled by the amplifier.

SUMMARY OF THE INVENTION

It is an object of the present invention to improve the temperature range for stable operation of a flueric partial pressure sensor such as is disclosed in EP-A-No. 0,036,285 and U.S. Pat. No. 4,407,153.

Accordingly, in meeting this object, the present invention provides a flueric partial pressure sensor including a flueric bridge having two legs, one of said legs being adapted for sensing a reference gas and the other said leg being adapted for sensing a sample-gas mixture, each leg including a linear flow resistor and an orifice flow resistor in series, a pressure signal outlet connected in each bridge leg at a position between the linear flow resistor and the orifice flow resistor, a flueric laminar flow proportional amplifier connected to said pressure signal outlets, a flueric aspirator connected for drawing reference gas and sample-gas mixture through the respective bridge legs and for operating the flueric amplifier by way of a power line conjoined with the bridge legs at a common outlet to the flueric aspirator, a pressurised gas delivery line including a pressure reducing valve for delivering pressurised working gas to operate the flueric aspirator, and temperature-responsive means adapted to vary suction applied by the flueric aspirator with temperature change whereby the velocity of gas flowing through main power jets of the flueric amplifier is controlled to maintain the working Reynolds number of the main power jets within a range which provides stable operation of the amplifier.

In one embodiment of the invention the temperature-responsive means may comprise temperature-sensitive adjustment means adapted to adjust the pressure reducing valve to vary the flueric aspirator working gas pressure with change in temperature whereby the suction applied by the flueric aspirator is respectively increased or decreased with increasing or decreasing temperature.

The temperature-sensitive adjustment means may be adapted to vary the working length of a spring with temperature change whereby the pressure in a control pressure chamber of the pressure reducing valve is adjusted appropriate to increasing or decreasing working gas pressure.

The temperature-sensitive adjustment means may be located between one end of the spring and an end of a threaded adjuster adapted for use in manual setting of the spring working length.

Such temperature-sensitive adjustment means may comprise a rubber block, a bimetallic washer or stack of washers, or other means which varies its length with temperature change.

In another embodiment of the invention the temperature-responsive means may alternatively or additionally comprise a temperature-sensitive bleed valve incorporated in the common outlet of the bridge legs and amplifier power line for control of the suction applied by the flueric aspirator with temperature change.

The temperature-sensitive bleed valve may comprise a valve body and a valve member manufactured from materials having differential rates of thermal expansion whereby a flow of ambient air drawn through the valve by the flueric aspirator varies with temperature change.

The temperature-sensitive bleed valve may comprise a valve body manufactured from a material having a high coefficient of thermal expansion and a valve mamber manufactured from a material having a low coefficient of thermal expansion whereby with increasing temperature the valve body expands to a greater extent than the valve member so that a valve seat provided in the valve body is moved towards a valve head provided on the valve member to restrict an inlet for ambient air drawn through the valve body by the flueric aspirator.

Alternatively, the temperature-sensitive bleed valve may comprise a valve body and a valve member manufactured from a material having a low coefficient of thermal expansion, and a temperature-expansion member manufactured from a material having a high coefficient of thermal expansion housed in the valve body for co-operation with the valve member so as to move the valve member towards increasingly restricting the flow of air drawn through the valve body by the flueric aspirator with increasing temperature.

In preferred embodiments of the invention, pressure reducing means, which may comprise a linear flow resistor or an orifice flow resistor, are incorporated in a supply inlet to the main power jets of the flueric amplifier to improve stability at the low temperature end of the working range.

BRIEF DESCRIPTION OF THE DRAWINGS

The invention will now be further described by way of example and with reference to the accompanying drawings, in which:

FIG. 5 is a cross-section through an alternative temperature-sensitive bleed valve suitable for use in the embodiment of FIG. 3.

DETAILED DESCRIPTION OF THE DRAWINGS

As hereinbefore described a flueric partial pressure sensor with which the present invention is concerned is disclosed in EP-A-No. 0,036,285 and corresponding U.S. Pat. No. 4,407,153. Tests carried out in an altitude chamber to establish if the sensor was suitable for use over an extended temperature range showed the oxygen concentration values output by a MSOGS controlled by the sensor to be unpredictable at temperatures below $-5°$ C. and for some sensors even below $0°$ C. Not only were these values unpredictable but they were also frequently outside of the permissible range for maintaining the oxygen partial pressure in oxygen-enriched air delivered by the MSOGS within limits required for breathing by aircrew.

It was known that the Reynolds number for the main power jets of a flueric amplifier as embodied in the flueric partial pressure sensor becomes critical at not much over 1000 so that the flow in the internal passages of the amplifier is turbulent rather than laminar when this critical number is exceeded.

Mathematical calculations of the Reynolds number for the main power jets at a known working pressure of about 10.5 kPa (1.5 psi) showed that the Reynolds number increases as temperature decreases. This is a result of the increase in density and decrease in viscosity of air with decreasing temperature. The Reynolds number is further increased with decreasing altitude (i.e. increasing pressure).

Conversely, Reynolds number was shown to decrease with increasing altitude and temperature so that the amplifier output signal becomes increasingly weak with reduced gain.

Performance of the flueric aspirator was shown to be insensitive to temperature change but sensitive to variation in flow. It was considered that if the secondary flow demand, i.e. the flow at the conjoined outlets of the bridge legs and amplifier power line, could be varied in response to temperature change then this could be used to vary the flow through the main power jets of the amplifier. Since Reynolds number varies with velocity then by increasing the flow through the main power jets with rising temperature it should be possible to increase the Reynolds number relative to the value it would otherwise be.

A flueric partial pressure sensor embodying such an improvement will now be described with reference to FIGS. 1 and 2.

Figure 1:
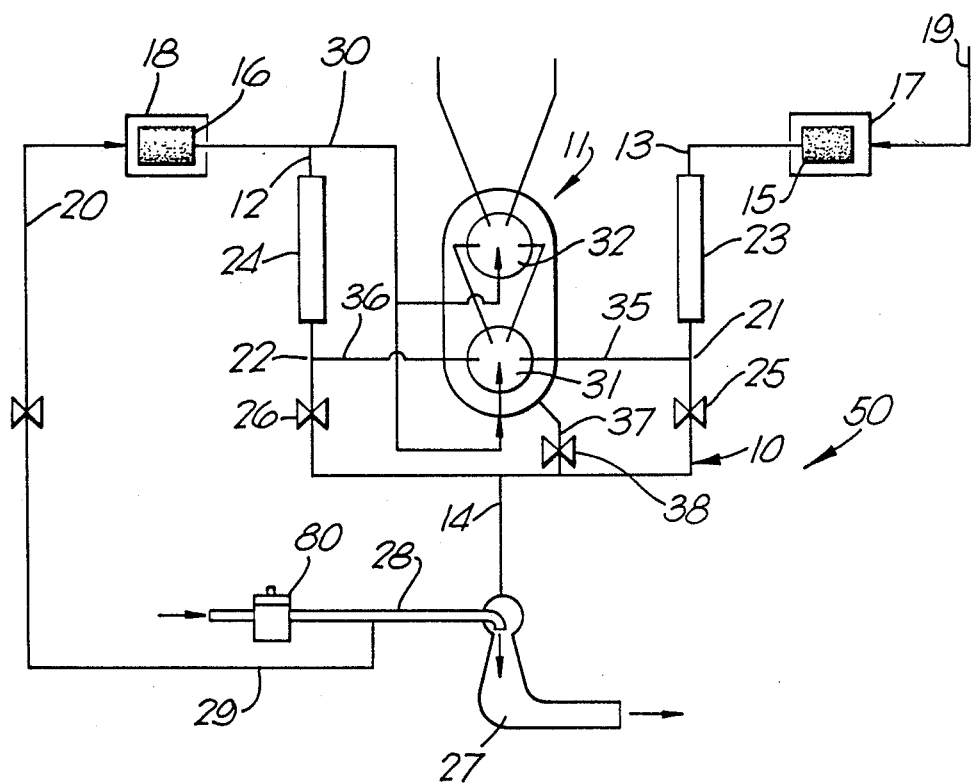
FIG. 1 is a diagrammatic illustration of a flueric partial pressure sensor in accordance with one embodiment of the present invention.

Referring first to FIG. 1, a flueric partial pressure of oxygen sensor 50 comprises a flueric bridge partial pressure sensor 10 and a suitably matched two stage high input impedance flueric laminar flow proportional amplifier 11, the sensor 10 being arranged to provide a constant output signal in terms of differential pressure, at varying altitudes for a predetermined constant oxygen partial pressure value. The sensor 10 is designed to operate with a supply pressure of 25 kPa (3 psi) and comprises a reference gas inlet leg 12 for the passage of air and a sample-gas inlet leg 13 for the passage of a gaseous mixture comprising oxygen-enriched air delivered by a MSOGS (not shown). The two legs conjoin to discharge from a single outlet 14. The sample-gas inlet leg 13 is provided at its entry with a filter 15 that is protected against extraneous contamination by a shroud 17 which connects to a sample-gas supply line 19, whilst a pressure signal outlet 21 is provided in the leg 13 at a position intermediate a linear resistor 23 and an orifice resistor 25 which is downstream thereof. The reference gas inlet leg 12 is arranged in a similar manner to that of the sample-gas inlet leg 13 and includes the following corresponding components, a filter 16, a shroud 18 connected to a reference gas supply line 20, and a pressure signal outlet 22, intermediate a linear resistor 24 and an orifice resistor 26.

Reference gas and sample-gas mixture are drawn through the respective bridge legs 12, 13 by connecting the outlet 14 to a flueric aspirator or ejector 27 arranged for operation in the manner of a jet pump by a clean dry gas which is conveniently a bleed of pressurised air from the compressor stage of an aircraft engine supplied by way of a pressure reducing valve 80 and a delivery line 28. A conduit 29 is connected to the delivery line 28 for feeding the reference gas supply line 20. A branch conduit 30 is connected to the leg 12 between the filter 16 and linear resistor 24 for supplying air to main power jets 31 and 32 of the flueric amplifier 11.

The pressure signal outlets 21 and 22 in the bridge legs 13 and 12, respectively, are connected by respective conduits 35 and 36 to the amplifier 11 in its two regions of pressure that effect control of the direction of the first stage main jet 31. A power line 37 for operating the amplifier 11 connects the amplifier by way of the discharge outlet 14 to the flueric aspirator 27. The power line includes an orifice resistor 38 by which means the controlling pressure and sensitivity of the sensor 50 is predetermined within an available range.

In accordance with the present invention the sensor 50 is characterised by temperature-responsive means which in this embodiment comprise temperature-sensitive adjustment means for controlling the pressure of working air supplied by the pressure reducing valve 80 to the aspirator in accordance with temperature whereby the pressure is increased with increasing temperature.

One embodiment of a pressure reducing valve including temperature-sensitive adjustment means will now be described with reference to FIG. 2 of the accompanying drawings.

Figure 2:
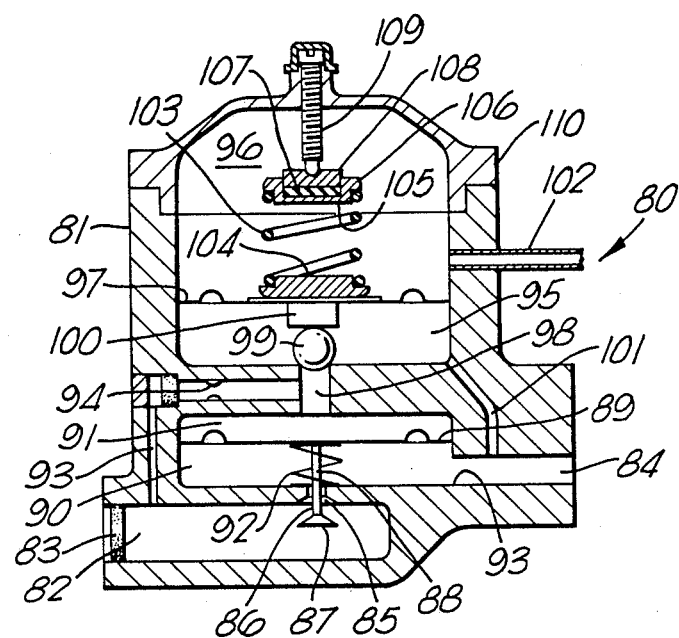
FIG. 2 is a schematic illustration showing the internal arrangement of a pressure regulating valve suitable for use in the flueric partial pressure sensor of FIG. 1.

A pressure reducing valve 80 comprises a valve body 81 providing an inlet 82 protected by a filter 83 for receiving a supply of pressurised air, and an outlet 84 for delivering air at a required working pressure to the aspirator by way of a delivery line (not shown in FIG. 2). Air entering the inlet 82 passes to the outlet 84 by way of a valve port 85. Flow of air through the port 85 is regulated by a main valve member 86 comprising a valve head 87 disposed on the inlet side of the port 85 and projecting a valve stem 88 through the port 85 to attachment with a diaphragm 89. The diaphragm 89 divides a supply pressure chamber 90 from a control pressure chamber 91. A compression spring 92 acting between the diaphragm 89 and a wall 93 of the delivery pressure chamber 90 urges the diaphragm to move the main valve member 86 towards closing the port 85. Air is supplied from the inlet 82 to the control pressure chamber 91 by way of a passageway 93 which includes a restricted orifice 94.

The valve 80 further comprises a control pressure regulating chamber 95 divided from a datum pressure chamber 96 by a diaphragm 97. The control pressure regulating chamber 95 communicates with the control pressure chamber 91 by way of a port 98 arranged for closure by a pilot ball valve member 99 held by a seat 100 carried by the diaphragm 97. A passageway 101 connects the control pressure regulating chamber 95 with the outlet 84.

A pressure sensing line 102 communicates the datum pressure chamber 96 with pressure ambient to the flueric partial pressure sensor which is that pressure external of the shrouded filters in the inlet lines to the bridge legs and into which the flueric aspirator discharges. A regulating compression spring 103 provided internally of the chamber 96 and acts between a pad 104 which contacts a plate on the diaphragm 97 and a pad 105 having a recess 106 in that end face which is disposed away from the spring 103. Temperature-sensitive adjustment means comprising a rubber block 107 is retained in the recess 106 by a small pad 108 which is a sliding fit in the recess. The outer face of the pad 108 contacts one end of a threaded adjuster 109 which is screwed into an end cover 110 of the pressure reducing valve. The adjuster 109 is used to set the working length of the regulating spring 103.

Before commencement o operation the main valve member 86 is held by the action of the compression spring 92 on the diaphragm 89 in a position in which the valve head 87 closes or very nearly closes the port 85. On start up pressurised air enters the inlet 82 of the valve 80 and the pressure difference across the main valve member 86 acts to more firmly close the valve head 87 with the port 85. Some of the gas in the inlet then flows through the passageway 93 and by way of the restrictor 94 into control pressure chamber 91. The pressure in datum pressure chamber 96 acting on the upper surface area of the diaphragm 97 combines with the force exerted by the regulating spring 103 to hold the pilot ball valve member 99 in a position closing the port 98.

As pressure builds up in control pressure chamber 91 it acts over the face of the diaphragm 89 to overcome the closing force applied to the main valve member 86 by the combined action of the spring 92 and inlet air pressure acting on the face of the valve head 87, and moves the main valve member 86 towards opening the port 85 so as to permit air to flow from the inlet 82 into the delivery pressure chamber 90 and then to the outlet 84. Pressure then builds up in the outlet 84 and the delivery line connecting the outlet to the flueric aspirator due to the impedance of the aspirator. This pressure build up is sensed in both the delivery pressure chamber 90 where it is effective on the undersurface to the diaphragm 89 and in the control pressure regulating chamber 95 where it is effective on the undersurface of the diaphragm 97.

The pressure build up in control pressure regulating chamber 95 is effective to overcome the opposing preset downward force applied by the regulating spring 103 and the pressure in datum pressure chamber 96 acting over the upper surface area of the diaphragm 97 to lift the diaphragm 97. Lifting of the diaphragm 97 allows the pressure in control pressure chamber 91 to lift the pilot ball valve member 99 off its seat permitting air to leak from the control pressure chamber 91 to the control pressure regulating chamber 95 and then to the outlet 84 by way of passageway 101. This curtails the increasing pressure building up in the control pressure chamber 91 which was acting to further open the valve member 86 and the build up of pressure in the delivery pressure chamber tends to move the valve member 86 towards closing the port 85 until a steady balance is established between upward and downward forces which dictates the operating position of the valve member 86 and the controlling value of the differential pressure above the value of the datum pressure.

An increase in temperature during operation is effective to cause the rubber block 107 to expand so as to reduce the working length of the regulating spring 103 and further increase the downward force applied by the regulating spring towards moving the pilot valve member 99 to close the port 98. This allows pressure in the control pressure chamber 91 to increase which in turn acts to open further the main valve member 86 so permitting an increased flow of air through the port 85. This increased flow of air from the inlet to outlet builds up the pressure in the outlet and delivery line until a new steady balance is established for operation of the valve at the higher temperature.

The increase in the pressure of working air delivered to the flueric aspirator acts to increase the suction applied by the aspirator and so varies the flow through the bridge legs and the main power jets of the flueric amplifier as to the increase the velocity of the air flowing through the jets thereby maintaining the value of the working Reynolds number of the jets which would otherwise tend to fall with increasing temperature.

Figure 3:
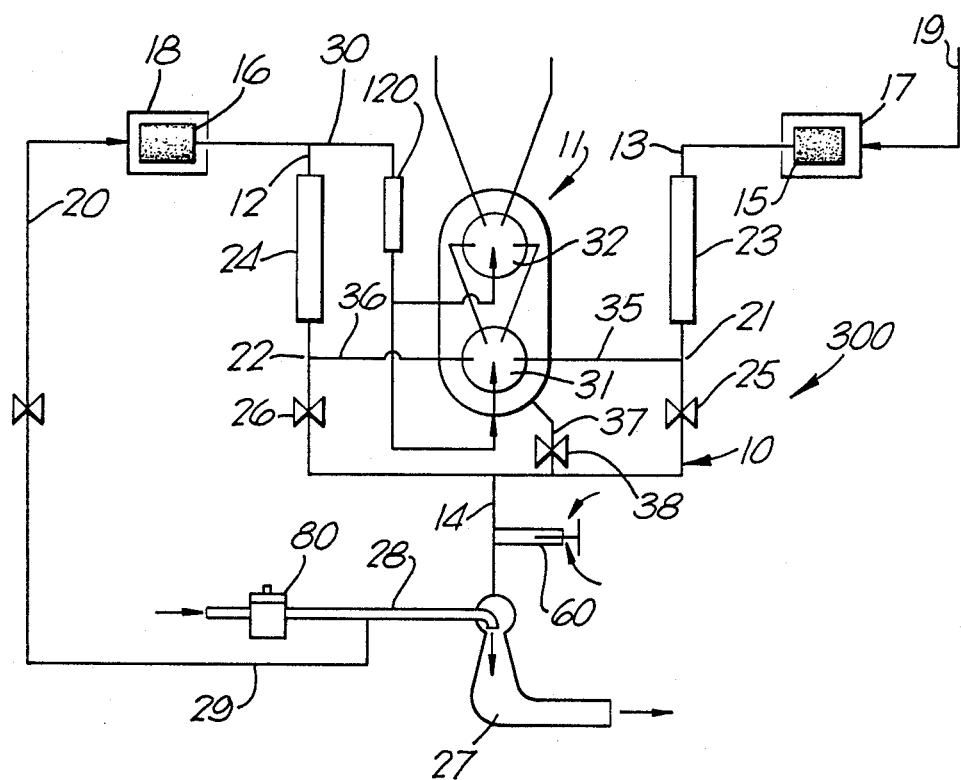
FIG. 3 is a diagrammatic illustration of a flueric partial pressure sensor in accordance with another embodiment of the invention.

A flueric partial pressure sensor 300 in accordance with another embodiment of the present invention is shown in FIG. 3. This sensor 300 is similar to the sensor 50 shown in FIG. 1 but the temperature-responsive means comprises a temperature-sensitive bleed valve 60 which is introduced into the conjoined outlet 14 of the bridge legs 12, 13, and amplifier power line 37. It is preferred that the temperature-sensitive bleed valve 60 complement a temperature-sensitive reducing valve 80 in providing temperature-responsive control of the suction applied by the aspirator 27. However, the temperature-sensitive bleed valve 60 may alone constitute the temperature-responsive means in which case the pressure reducing valve will have no temperature sensitivity.

One embodiment of a temperature-sensitive bleed valve 60 suitable for incorporation in the outlet 14 will now be described with reference to FIG. 4 of the accompanying drawings.

Figure 4:
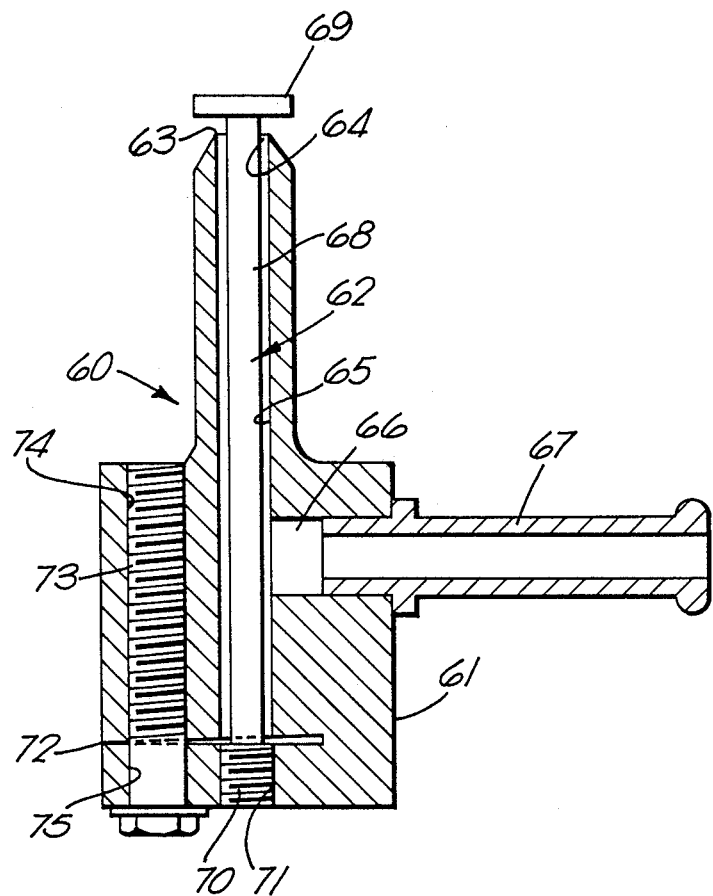
FIG. 4 is a cross-section through a temperature-sensitive bleed valve suitable for use in the embodiment of FIG. 3.

The temperature-sensitive bleed valve 60 shown in FIG. 4 comprises a valve body 61 manufactured from a material having a high coefficient of thermal expansion, such as an aluminium alloy, and a valve member 62 manufactured from a material having a lower coefficient of thermal expansion than that of the aluminium alloy such as a controlled expansion nickel iron alloy. The valve body 61 provides a valve seat 63 at an inlet 64 to a right angle bore 65 extending through the valve body to have its opposite end 66 entered by a tubular connector member 67 by which the bleed valve 60 is connected into the conjoined outlet of the bridge legs and amplifier power line. The valve member 62 has a valve stem 68 which extends through one leg of the right angle bore 65 to project externally of the inlet 64 and terminate at a valve head 69 adapted for cooperation with the valve seat 63. The valve stem is of smaller diameter dimension than the diameter dimension of the bore 65 whereby a passageway is provided between the valve stem and the bore wall. The opposite end 70 of the valve stem 68 is threaded and engages in a threaded bore 71 provided in the valve body 41 at the opposite end of the bore leg. The threaded end 70 of the valve stem 68 is made to be a tight fit with the threaded bore 71 but to further lock the valve stem against longitudinal movement along the axis of the bore leg the valve body has a slot 72 extending through the threaded bore 71 from one face of the valve body. The slot faces are pinched towards each other to lock the threads of the threaded bore 71 with the valve stem threads by a bolt 73 which is screwed into a threaded bore 74 extending parallel to the threaded bore 71 in the valve body 61 and which is separated by the slot 72 from a plain bore 75 through which the neck of the bolt 73 passes.

In operation of a flueric partial pressure sensor 300 having temperature-responsive means comprised by both a temperature-sensitive bleed valve 60 and a temperature-sensitive pressure reducing valve 80, the valve body 61 of the temperature-sensitive bleed valve 60 expands with rising temperature to a greater extent than the valve member 62 so that the valve seat 63 moves towards the valve head 69 thereby reducing the flow of ambient air drawn into the inlet 64 by the flueric aspirator 27. At the same time higher suction is applied by the flueric aspirator to the conjoined outlet 14 as the aspirator working air pressure delivered by the temperature-sensitive pressure reducing valve increases with rising temperature. As the flow of ambient air drawn into the bleed valve 60 decreases, this higher suction is increasingly effective in the bridge legs and, also, in the power line 37 to the flueric amplifier 11 so that the velocity of the air flowing through the main power jets 32 and 34 of the amplifier increases to at least offset a fall in the working Reynolds number of the amplifier main jets which would otherwise occur with rising temperature.

As temperature falls towards the low end of the range the inlet 64 is increasingly opened by movement of the valve seat 63 away from the valve head 69 allowing more air to be drawn into the inlet 64 by the flueric aspirator 27. At the same time the pressure of the working air delivered by the temperature-sensitive pressure reducing valve falls so that the suction applied to the bridge legs and the power line 37 of the amplifier 11 by the flueric aspirator is reduced. This decreases the velocity of the air flowing through the main power jets of the amplifier and hence the working Reynolds number for the jets is kept below the critical value at which flow would become turbulent.

Another embodiment of a temperature-sensitive bleed valve 60 suitable for incorporation in the outlet 14 is shown in FIG. 5. The valve 60 comprises a hollow cylindrical shaped main body 500 manufactured from a material having a low coefficient of thermal expansion such as a controlled expansion nickel iron alloy. The main body 500 is open at one end 501 and closed at the opposite end 502 by an end wall 503 which projects a threaded union 504 for connection of the valve into the outlet 14. A small diameter bore 505 extends through the threaded union 504 and end wall 503 into alignment with a bore 506 of similar diameter in a PTFE temperature-expansion plug 507 housed internally of the main body 500. The expansion plug 507 is of smaller diameter than the internal surface diameter of the main body 500 over a major portion of its length but at that end which abuts with the internal surface of the end wall 503 the expansion plug has an integral flange 508 of diameter such that it is a sliding fit with the internal surface of the main body. The flange 508 is provided with a circumferentially extending groove 509 in which is seated an O-ring 510 that provides a seal between the flange and the internal surface of the main body.

A top hat member 511 sits on a reduced diameter end portion 512 of the expansion plug opposite to the flanged end 508. A flange 513 of the top hat member is of such diameter as to be a sliding fit with the internal surface of the main body. The end face of the expansion plug is sealed with the internal face of the top hat end wall 514. An orifice 515 is provided in the end wall 514 in axial alignment with the bore 506 in the expansion plug 507.

An end plug 516 is located in the open end 501 of the main body and retained therein by a retaining ring 517. An O-ring 518 seated in a circumferentially extending groove 519 in the end plug 516 provides a seal between the plug and internal surface of the main body. A compression spring 520 extends between the flange 513 of the top hat member 511 and that end face 521 of the end plug which faces into the main body.

A threaded needle valve member 522 extends through the end plug 516 and is locked therewith by a locking nut 523 on that end 524 of the valve member which projects externally of end plug and main body. The opposite end 525 of the valve member 522 is tapered and projects into the orifice 515 in the end wall 514 of the top hat member 511.

Four vent holes 526 (only two being seen in FIG. 5) in the wall of the main body are equally spaced around the circumference thereof and are positioned inwardly of the end 501 of the main body so as to have their centres in approximate alignment with the end wall 514 of the top hat member 511. Each vent hole 526 is covered by a wire filter 527.

The top hat member 511, end plug 516 and needle valve member 522 are all manufactured from stainless steel.

In operation the temperature-sensitive bleed valve is connected into the conjoined outlet of the bridge legs and amplifier power line so that the flueric aspirator is effective to draw ambient air into the valve through the vent holes 526. The PTFE temperature-expansion plug 507 has a high coefficient of thermal expansion so that it expands and contracts in length to a much greater extent that the other component parts of the bleed valve, in particular the main body 500, with temperature changes within the working temperature range of $-40°$ C. to $+70°$ C. With increasing temperature the expansion plug 507 expands in length and moves the top hat member 511 against the compression spring 520 towards the end plug 516 so that the needle valve 522 increasingly restricts the orifice 515 in the end wall 514 of the top hat member. This increasing restriction reduces the flow of ambient air to the flueric aspirator by way of the vent holes 526, the orifice 515, the small diameter bores 506, 505, and the common outlet 14, so that suction applied by the aspirator is increasingly effective in the bridge legs and the power line of the flueric amplifier thereby increasing the velocity of the air flowing through the main power jets of the amplifier. Conversely, with decreasing temperature, the expansion plug contracts in length and the top hat member is urged by the compression spring away from the end plug so that the orifice in the end wall of the top hat is increasingly opened to allow the flueric aspirator to draw in more ambient air thereby reducing the suction applied by the aspirator to the bridge legs and power line of the amplifier so that the velocity of the air flowing through the main power jets of the amplifier decreases.

Operation of a flueric partial pressure sensor in accordance with the present invention may be further improved at the low temperature end by incorporating pressure reducing means such as may be provided by a linear flow resistor comprising a capillary resistor 120 (reference FIG. 3) in the conduit 30 supplying air to the main power jets 31 and 32 of the amplifier 11. This resistor reduces the pressure of the air flowing to the main power jets which further reduces the velocity of the air flowing through the main power jets so as to keep the working Reynolds number of the main power jets low and assist in maintaining the amplifier stable at the low temperature end of the range. The value of the resistor 90 is chosen so as to maximise the beneficial effect at low temperature whilst not adversely affecting operation of the amplifier at the high temperature end of the range.

It will be appreciated, of course, that the capillary resistor could be replaced by an orifice flow resistor (not shown) of suitable resistance value.

Tests carried out on a flueric partial pressure sensor having a pressure reducing valve including temperature-sensitive means for varying the working pressure of air delivered by the pressure reducing valve, a temperature-sensitive bleed valve incorporated in the conjoined outlet of the bridge legs and amplifier power line, and a resistor in the inlet line to the flueric amplifier main power jets, have shown improvements are obtained at both ends of the temperature range. At the high temperature end, i.e. approaching $+70°$ C., the working Reynolds number for the amplifier main power jets is increased over the value it would otherwise be whilst at the low temperature the working Reynolds number is reduced allowing operation of the sensor down to $-40°$ C.

Whilst the flueric partial pressure sensor hereinbefore described with reference to the accompanying drawings embodies a two stage flueric laminar flow proportional amplifier, the invention is not limited thereto, being equally applicable to a sensor having a single stage amplifier.

What is claimed is:
1. A flueric partial pressure sensor comprising a flueric bridge having two legs, one of said legs being adapted for sensing a reference gas and the other said leg being adapted for sensing a sample-gas mixture, each leg including a linear flow resistor and an orifice flow resistor in series, a pressure signal outlet connected in each bridge leg at a position between the linear flow resistor and the orifice flow resistor, a flueric laminar flow proportional amplifier connected to said pressure signal outlets, a flueric aspirator connected for drawing reference gas and sample-gas mixture through the respective bridge legs and for operating the flueric amplifier by way of a power line conjoined with the bridge legs at a common outlet to the flueric aspirator, a pressurized gas delivery line including a pressure reducing valve for delivering pressurized working gas to operate the flueric aspirator, the pressure reducing valve having temperature-responsive means comprising temperature-sensitive adjustment means adapted to adjust the pressure reducing valve to increase the pressure of working gas delivered to the flueric aspirator with increasing temperature whereby suction applied by the flueric aspirator at the common outlet is increased thereby increasing the velocity of gas flowing through the main power jets of the flueric amplifier to maintain the working Reynolds number of the main power jets within a range which provides stable operation of the amplifier.

2. A flueric partial pressure sensor as claimed in claim 1, wherein the temperature-sensitive adjustment means is adapted to vary the working length of a spring with temperature change whereby pressure in a control pressure chamber of the pressure reducing valve is adjusted appropriate to increasing or decreasing working gas pressure.

3. A flueric partial pressure sensor as claimed in claim 2, wherein the temperature-sensitive adjustment means is located between one end of the spring and an end of a threaded adjuster adapted for use in manual setting of the spring working length.

4. A flueric partial pressure sensor as claimed in claim 2, wherein the temperature-sensitive adjustment means comprises a rubber block which varies its length with temperature change.

5. A flueric partial pressure sensor as claimed in claim 1, wherein the temperature-responsive means comprise a temperature-sensitive bleed valve incorporated in the common outlet of the bridge legs and amplifier power line for control of suction applied by the flueric aspirator with temperature change.

6. A flueric partial pressure sensor as claimed in claim 5, wherein the temperature-sensitive bleed valve comprises a valve body and a valve member manufactured from materials having differential rates of thermal expansion whereby a flow of ambient air drawn through the valve by the flueric aspirator varies with temperature change.

7. A flueric partial pressure sensor as claimed in claim 6, wherein the temperature-sensitive bleed valve comprises a valve body manufactured from a material having a high coefficient of thermal expansion and a valve member having a low coefficient of thermal expansion whereby with increasing temperature the valve body expands to a greater extent than the valve member so that a valve seat provided in the valve body is moved towards a valve head provided on the valve member to restrict an inlet for ambient air drawn through the valve body by the flueric aspirator.

8. A flueric partial pressure sensor as claimed in claim 6, wherein the temperature-sensitive bleed valve comprises a valve body and a valve member manufactured from a material having a low coefficient of thermal expansion, and a temperature-expansion member manufactured from material having a high coefficient of thermal expansion housed in the valve body for cooperation with the valve member so as to move the valve member towards increasingly restricting the flow of air drawn through the valve body by the flueric aspirator with increasing temperature.

9. A flueric partial pressure sensor as claimed in claim 1, wherein pressure reducing means are incorporated in a supply inlet to the main power jets of the flueric amplifier.

10. A flueric partial pressure sensor as claimed in claim 9, wherein the pressure reducing means comprise a linear flow resistor.

11. A flueric partial pressure sensor comprising a flueric bridge having two legs, one of said legs being adapted for sensing a reference gas the other said leg being adapted for sensing a sample-gas mixture, each leg including a linear flow resistor and an orifice flow resistor in series, a pressure signal outlet connected in each bridge leg at a position between the linear flow resistor and the orifice flow resistor, a flueric laminar flow proportional amplifier connected to said pressure signal outlet, a gas supply inlet line connected to main power jets of the flueric amplifier, pressure reducing means incorporated in said supply inlet line, a flueric aspirator connected for drawing reference gas and sample-gas mixture through the respective bridge legs and for operating the flueric amplifier by way of a power line conjoined with the bridge legs at a common outlet to the flueric aspirator, a pressurized gas delivery line including a pressure reducing valve for delivering pressurized working gas to operate the flueric aspirator, the pressure reducing valve having temperature-responsive means comprising temperature sensitive adjustment means adapted to adjust the pressure reducing valve to increase the pressure of working gas delivered to the flueric aspirator with increasing temperature whereby suction applied by the flueric aspirator at the common outlet is increased thereby increasing the velocity of gas flowing through the main power jets of the flueric amplifier to maintain the working Reynolds number substantially constant.

12. A flueric partial pressure sensor as claimed in claim 11, wherein the pressure reducing means comprises a linear flow resistor.

* * * * *